United States Patent [19]

Schönafinger et al.

[11] Patent Number: 4,987,134
[45] Date of Patent: Jan. 22, 1991

[54] THIENYLPIPERAZINES, THE USE THEREOF AND PHARMACEUTICALS CONTAINING THESE

[75] Inventors: Karl Schönafinger, Alzenau; Rudi Beyerle, Frankfurt; Ursula Schindler, Mörfelden-Walldorf; Bernd Jablonka, Oberursel, all of Fed. Rep. of Germany; Jeffery Troke, Pagnell, England

[73] Assignee: Cassella Aktiengesellschaft, Frankfurt, Fed. Rep. of Germany

[21] Appl. No.: 494,606

[22] Filed: Mar. 16, 1990

[30] Foreign Application Priority Data

Mar. 22, 1989 [DE] Fed. Rep. of Germany ....... 3909379

[51] Int. Cl.$^5$ .................. A61K 31/495; C07D 409/04
[52] U.S. Cl. ..................................... 514/252; 544/379
[58] Field of Search .......................... 544/379; 514/252

[56] References Cited

U.S. PATENT DOCUMENTS

| | | | |
|---|---|---|---|
| 4,407,797 | 10/1983 | Cortrel et al. | 544/379 |
| 4,598,079 | 7/1986 | Beyerle et al. | 514/252 |
| 4,898,866 | 2/1990 | Schönafinger et al. | 544/379 |

FOREIGN PATENT DOCUMENTS 0181152 5/1986 European Pat. Off. .

*Primary Examiner*—Frederick E. Waddell
*Assistant Examiner*—James H. Turnipseed
*Attorney, Agent, or Firm*—Perman & Green

[57] ABSTRACT

The present invention relates to thienylpiperazines of the general formula I

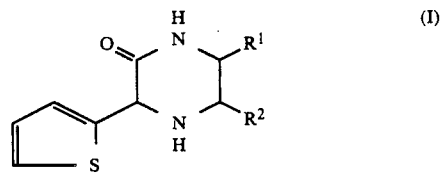

in which $R^1$ denotes hydrogen or double-bonded oxygen and $R^2$ denotes hydrogen or double-bonded oxygen, with $R^1$ and $R^2$ not both having the same meaning, as well as the pharmaceutically tolerated salts thereof, process for the preparation thereof, the use thereof, and pharmaceuticals containing these and the preparation thereof.

5 Claims, No Drawings

THIENYLPIPERAZINES, THE USE THEREOF AND PHARMACEUTICALS CONTAINING THESE

BACKGROUND OF THE INVENTION

1. Field of the Invention

The present invention relates to novel thienylpiperazine pharmaceutical compounds and to processes for the preparation of such compounds. The invention also relates to pharmaceutical compositions containing the present compounds, and to the preparation and use of such compositions for the treatment of disorders of brain functions or for controlling cerebral aging processes.

1. Description of the Art

The novel compounds and compositions of the present invention have been found to be considerably superior to hitherto known compounds used for similar purposes, such as piracetam, aniracetam and oxiracetam, which are not thienylacetic acid derivatives.

The closest known chemically-related thienylacetic acid compounds are disclosed in U.S. Pat. No. 4,598,079.

SUMMARY OF THE INVENTION

The present invention relates to thienylpiperazines of the general formula I

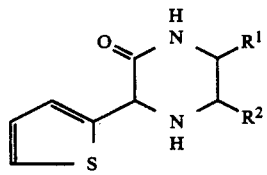

in which $R^1$ denotes hydrogen or double-bonded oxygen and $R^2$ denotes hydrogen or double-bonded oxygen, with $R^1$ and $R^2$ not both having the same meaning, as well as the pharmaceutically tolerated salts thereof. Hence the present invention embraces 3-(2-thienyl)piperazine-2,5-dione of the formula Ia

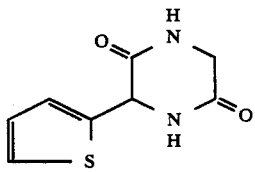

and 3-(2-thienyl)piperazine-2,6-dione of the formula Ib

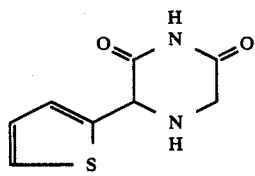

as well as pharmaceutically tolerated salts thereof. Pharmaceutically tolerated salts are preferably acid addition salts, particularly preferably the hydrochlorides. The compounds of the general formula I can be prepared by cyclization of the compound of the formula II

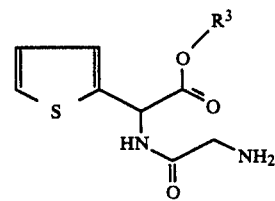

in which $R^3$ denotes $(C_1-C_4)$-alkyl, or by cyclization of the compound of the formula III

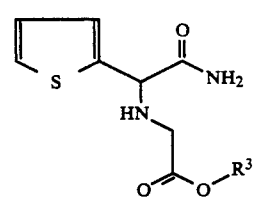

in which $R^3$ is as defined above, and, where appropriate, subsequent conversion into a pharmaceutically tolerated salt.

The cyclizations of the compounds of the formulae II and III are preferably carried out in a known manner by heating in a suitable solvent or by the catalytic action of acids or bases.

Suitable solvents are, in particular, alcohols such as, for example, methanol, ethanol, isopropanol, butanol, glycol, ether, such as, for example, dimethoxyethane or diethoxyethane, and toluene and xylene.

The temperature is preferably raised to 40° C. up to the boiling point of the solvent.

Acids or bases suitable for the cyclization are, in particular, hydrogen chloride, trifluoroacetic acid, toluenesulphonic acid, sodium acetate, sodium carbonate, sodium hydroxide, sodium hydride, sodamide.

The preparation of the compounds of the formula II starts from the thienylglycine esters of the general formula IV

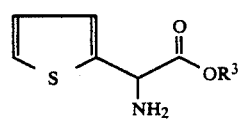

in which $R^3$ is as defined above. The latter are converted into the compounds of the formula II in a manner known per se by reaction with the mixed anhydride of the formula V

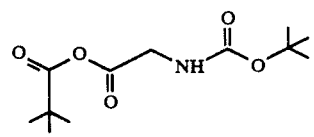

and subsequent hydrolysis.

The acylation with the mixed anhydride is preferably carried out in inert solvents, particularly preferably in DMF or ether. The reaction temperatures are preferably at −20° to +60° C. particularly preferably at −20° C. to room temperature. The hydrolysis is preferably carried out with acid, particularly preferably with hydrogen chloride or trifluoroacetic acid. The reaction temperatures in this case are preferably at 0° to 50° C., particularly preferably at room temperature.

In a preferred embodiment, the reaction product of the reaction between the compound of the general formula IV and the mixed anhydride of the formula V is converted directly, that is to say without isolation of the compound of the general formula II, into the compound of the formula Ia according to the invention.

The starting material for the preparation of the compounds of the formula II is the thienylglycinamide of the formula VI

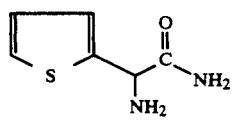

(VI)

which leads directly to the desired products by reaction with halogenoacetic esters of the general formula VII

(VII)

in which Hal denotes halogen, preferably bromine, and $R^3$ is as defined above, in a manner known per se. At reaction temperatures of, preferably, 0°–100° C., this entails use of, preferably, inert solvents, particularly preferably ether, DMF or DME.

The compounds of the formulae IV and VI can be obtained, for example, from 2-thienylglyoxylic acid, which can be bought, by esterification and amidation, respectively, or from the esters thereof, such as, for example, from ethyl 2-thienylglyoxylate, by transesterification and ammonolysis with ammonia, respectively, and subsequent reaction with hydroxylamine to give the corresponding oxime and reduction of the oxime. As an alternative to this, the compounds of the formulae IV and VI can also be prepared by esterification and amidation, respectively, of 2-thienylglycine, which can be bought.

Esterifications, transesterifications, amidations, ammonolysis, oxime formation and reduction are types of reactions which are known per se to those skilled in the art and described in all current textbooks of organic chemistry, for example in Houben-Weyl, "Methoden der Organischen Chemie" (Methods of Organic Chemistry).

The compound of the formula V is known and is advantageously prepared in situ from N-tert.-butoxycarbonylglycine and trimethylacetyl chloride.

Where the compounds of the general formula I according to the invention contain basic residues, they form acid addition salts with inorganic or organic acids. Suitable for forming acid addition salts of this type are inorganic and organic acids. Examples of suitable acids are: hydrogen chloride, hydrogen bromide, naphthalenedisulphonic acids, especially naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared as customary by combining the components, expediently in a suitable solvent or diluent. It is possible in the synthesis of the compounds of the general formula I for the acid addition salts to be produced first in the course of working up. The free compounds of the general formula I can be obtained if desired from the acid addition salts in a known manner, for example by dissolving or suspending in water and making alkaline, for example with sodium hydroxide solution, and subsequently isolating.

Where the compounds of the general formula I according to the invention have acidic groups, the latter can also be in salt form. The sodium, potassium and ammonium salts are preferred and can be obtained by reacting the acid form with appropriate bases.

The compounds of the general formula I according to the invention, and the pharmaceutically tolerated salts thereof, have valuable pharmacological properties. They have CNS activity, for example they display encephalotropic and nootropic effects and are used for the treatment of disorders of brain functions such as cerebral insufficiency, cerebral ageing processes, diminished memory efficiency as also occur in Alzheimer's disease or multiinfarct dementia or in diminished learning efficiency. Surprisingly, they are considerably superior to the hitherto known compounds acting in the same direction. They display an excellent activity in a variety of tests such as, for example, in the prolongation of survival time under sodium nitrite hypoxia (Gibsen and Bless, J. Neurochemistry 27, (1976)), in the improvement in nitrogen-induced hypoxia tolerance, where experimental animals are, after premedication with the investigated products, ventilated with pure nitrogen, and the prolongation of the period between starting ventilation and electrical neutrality of the electroencephalogram, and the lethality, are measured.

The products according to the invention also have very good activity in tests which are directly aimed at measuring learning and memory efficiency such as, for example, the known avoidance tests.

Testing in the tests mentioned, and in a number of others, reveals that the compounds according to the invention surprisingly have, in low doses, together with a low toxicity, a particularly beneficial profile of effects not present in this form in known products.

The following tables are intended to show this in detail:

(1) Scopolamine-induced amnesia in the mouse

Injection of a scopolamine dose of 3 mg/kg i.p. leads to an amnesia in a passive-avoidance learning test. Oral pretreatment with the compounds of the general formula I can, as the following table shows, significantly antagonize the experimentally induced amnesia. The known substance piracetam has, by comparison with this, only marginal activity.

| Compound of the formula | Dose mg/kg oral | Scopolamine amnesia % reversal of amnesia |
|---|---|---|
| Ia | 30 | 53 |
| Ib | 30 | 59 |
| Piracetam (comparison) | 30 | 18 |

(2) Ischaemia-induced amnesia in the Mongolian gerbil

Brief bilateral cerebral ischaemia (3–5 min) in the gerbil leads to a prolonged learning impairment in passive-avoidance learning. The learning impairment can be antagonized if the animals are treated intraperitoneally with the compounds of the general formula I immediately after the end of ischaemia. The table which follows indicates the dosages which elicit a half-maximum (about 50%) antagonism of the learning impairment. The compounds according to the invention show a pronounced superiority to the compounds of the state of the art.

| Compound of the formula | Dose mg/kg ip | Ischaemia-induced learning impairment % reversal of learning impairment |
|---|---|---|
| Ia | 1.00 | 46 |
| Ib | 3.00 | 46 |
| Aniracetam (comparison) | 30.00 | 45 |
| Oxiracetam (comparison) | 100.00 | 46 |

The compounds of the general formula I and the physiologically tolerated salts thereof thus represent an enrichment of pharmacy.

The compounds of the general formula I according to the invention and the pharmaceutically tolerated salts thereof can thus be used in humans as medicines, for example for controlling or preventing disorders based on an impairment of brain function, and for the treatment and prevention of cerebral ageing processes.

The compounds of the general formula I and the pharmaceutically tolerated salts thereof can be administered as medicines alone, mixed with one another or in the form of pharmaceutical preparations which allow enteral or parenteral administration and which contain as active ingredient an effective dose of at least one compound of the general formula I or of a salt thereof, in addition to customary pharmaceutically acceptable vehicles and additives. The preparations normally contain about 0.5 to 90% by weight of the therapeutically active compound.

The medicines can be administered orally, for example in the form of pills, tablets, lacquered tablets, coated tablets, granules, hard and soft gelatin capsules, solutions, syrups, emulsions or suspensions or aerosol mixtures. The administration can, however, also take place rectally, for example in the form of suppositories, or parenterally, for example in the form of injection solutions, or percutaneously, for example in the form of ointments or tinctures.

The pharmaceutical products are prepared in a manner known per se, using pharmaceutically inert inorganic or organic vehicles. It is possible to use for the preparation of pills, tablets, coated tablets and hard gelatin capsules, for example lactose, maize starch or derivatives thereof, talc, stearic acid or salts thereof etc. Examples of vehicles for soft gelatin capsules and suppositories are fats, waxes, semisolid and liquid polyols, natural or hardened oils etc. Examples of suitable vehicles for the preparation of solutions and syrups are water, sucrose, invert sugar, glucose, polyols etc. Examples of suitable vehicles for the preparation of injection solutions are water, alcohols, glycerol, polyols, vegetable oils etc.

The pharmaceutical products can, besides the active compounds and vehicles, also contain additives such as, for example, fillers, extenders, disintegrants, binders, lubricants, wetting agents, stabilizers, emulsifiers, preservatives, sweeteners, colorants, flavourings or aromatizing agents, thickeners, diluents, buffer substances, as well as solvents or solubilizers or agents to achieve a depot effect, as well as salts to alter the osmotic pressure, coating agents or antioxidants. They can also contain two or more compounds of the general formula I or the pharmacologically acceptable acid addition salts thereof and, in addition, one or more other therapeutically active substances.

Examples of other therapeutically active substances of this type are agents to promote blood flow, such as dihydroergocristine, nicergoline, buphenine, nicotinic acid and esters thereof, pyridylcarbinol, bencyclane, cinnarizine, naftidrofuryl, raubasine and vincamine; positive inotropic compounds such as digoxin, acetydigoxin, metildigoxin and lanato glycosides; coronary dilators such as carbocromen, dipyridamole, nifedipine and perhexiline, antianginal compounds such as isosorbide dinitrate, isosorbide mononitrate, glycerol nitrate, molsidomine and verapamil, $\beta$-blockers such as propranolol, oxprenolol, atenolol, metoprolol and penbutolol. In addition, the compounds can be combined with other substances with nootropic activity, such as, for example, piracetam, or substances with CNS activity, such as pirlindole, sulpiride etc.

The dosage can be varied within wide limits and should be adjusted in each individual case to the individual circumstances. In general, a daily dose of about 0.1 to 1 mg/kg, preferably 0.3 to 0.5 mg/kg, of body weight is appropriate on oral administration to achieve effective results, and the daily dose on intravenous administration is generally about 0.01 to 0.3 mg/kg, preferably 0.05 to 0.1 mg/kg, of body weight. The daily dose is normally divided into several, for example 2, 3 or 4, partial administrations, especially when relatively large amounts are administered. It may be necessary where appropriate, depending on individual behaviour, to deviate from the stated daily dose in an upward or downward direction. Pharmaceutical products normally contain 0.1 to 50 mg, preferably 0.5 to 10 mg, of active compound of the general formula I or of a pharmacologically acceptable salt thereof per dose.

Examples 1 and 2 which follow relate to the preparation of compounds of the general formula I, and Examples A to H relate to the production of preparations of compounds of the general formula I.

EXAMPLE 1

3-(2-Thienyl)piperazine-2,5-dione (a) Methyl 2-thienylaminoacetate HCl

Gaseous HCl is passed into a solution of 6.8 g of 2-thienylaminoacetic acid in 70 ml of methanol, and the mixture is heated at 50° C. for 6 h. The excess methanol and hydrochloric acid are stripped off in vacuo, and the solid residue is washed with methanol and dried in vacuo.

Yield: 5.9 g; melting point 179° C.

(b) Methyl 2-thienyl-N-tert.-butoxycarbonylaminoacetylaminoacetate

N-tert.-butoxycarbonylglycine (4.3 g) and 2.5 g of triethylamine are dissolved in 240 ml of tetrahydrofuran and cooled to −20° C. Then 2.9 g of trimethylacetyl chloride are added dropwise, and the mixture is stirred at −20° C. for 30 min. A solution of 5.6 g of the compound from Example 1a) and 2.5 g of triethylamine in 20 ml of dimethylformamide is added dropwise to this mixture. The cold bath is removed, and the mixture is stirred at room temperature for 2 h. The precipitate is filtered off with suction, and the filtrate is concentrated. The oily residue is dissolved in ethyl acetate, and the solution is washed twice with 100 ml of water each time, once with 100 ml of 5% strength sodium bicarbonate solution and once with 100 ml of 1 N citric acid and is dried over magnesium sulphate. An oily product remains after removal of the solvent.

Yield: 6.4 g; oil.

3-(2-Thienyl)piperazine-2,5-dione

A mixture of 6.4 g of methyl 2-thienyl-N-(tert.-butoxycarbonylaminoacetyl)aminoacetate and 200 ml of formic acid is stirred at room temperature for 15 h. The volatile fractions are stripped off in vacuo, and the residue is heated to boiling in a mixture of 80 ml of toluene and 300 ml of butanol under reflux for 3 h. The solvents are then removed in a rotary evaporator, and the residue is recrystallized from methanol.

Yield: 1.5 g; melting point 220° to 222° C.

Example 2

3-(2-Thienyl)piperazine-2,6-dione (a) 2-Thienylglyoxylamide 13.6 g of ammonia are passed into a cooled solution of 73.6 g of ethyl 2-thienylglyoxylate, and the resulting mixture is stirred at room temperature for 2 h. The solvent is stripped off in vacuo, and the residue is recrystallized from water:ethanol (80:20).

Yield: 40.3 g; melting point 86°-88° C.

(b) 2-Thienylhydroximinoacetamide

A mixture of 15.5 g of 2-thienylglyoxylamide, 75 ml of water, 75 ml of ethanol, 10.4 g of hydroxylamine hydrochloride and 24.6 g of sodium acetate is stirred at 40° C. for 5 h, the volatile fractions are stripped off in vacuo, and the residue is taken up in water. The product is extracted with ethyl acetate, and the organic phase is dried and concentrated. The residue is recrystallized from a little ethyl acetate.

Yield: 5.2 g; melting point 146°-149° C.

(c) 2-Thienylaminoacetamide

A mixture of 5.1 g of 2-thienylhydroximinoacetamide and 180 ml of methanol is hydrogenated in the presence of Raney nickel at 100° C./50 bar. After hydrogen uptake has ceased, the Raney nickel is filtered off with suction, the filtrate is concentrated, and the residue is recrystallized from diethyl ether.

Yield: 2.6 g; melting point 82°-84° C.

(d) 2-Thienyl-N-methoxycarbonylmethylaminoacetamide

A solution of 9.4 g of 2-thienylaminoacetamide (Example 2c), 10.1 g of methyl bromoacetate and 6.7 g of triethylamine in 100 ml of dimethoxyethane is boiled for 16 h. The residue remaining after concentration is partitioned between water and ethyl acetate. The ethyl acetate phase is dried, boiled with active charcoal, filtered and concentrated. The residue is recrystallized from ethyl acetate.

Yield: 2.7 g.

(e) 3-(2-Thienyl)piperazine-2,6-dione

Sodium hydride (1.6 g; 50% in white oil) is added in portions to a solution of 4.6 g of 2-thienyl-N-methoxycarbonylmethylaminoacetamide in 50 ml of anhydrous xylene, and the mixture is boiled for 15 h. 1.8 g of glacial acetic acid are added and then the mixture is filtered hot with suction through Celite, the filtrate is cooled in an ice bath, and the solid is filtered off with suction, washed with ether and dried.

Yield: 1.0 g. melting point 128° to 129° C.

EXAMPLE A

Emulsions containing 3 mg of active compound per 5 ml can be produced using the following formula:

| | |
|---|---|
| Active compound | 0.06 g |
| Neutral oil | q.s. |
| Sodium carboxymethylcellulose | 0.6 g |
| Polyoxyethylene stearate | q s. |
| Pure glycerol | 0.2 to 2 g |
| Perfumes | q.s. |
| Water (demineralized or distilled) | ad 100 ml |

EXAMPLE B

Tablets can be produced using the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

EXAMPLE C

The following composition is suitable for the production of soft gelatin capsules containing 5 mg of active compound per capsule:

| | |
|---|---|
| Active compound | 5 mg |
| Mixture of triglycerides from coconut oil | 150 mg |
| Capsule contents | 155 mg |

EXAMPLE D

The following formulation is suitable for the

| | |
|---|---|
| Active compound | 3 mg |
| Maize starch | 100 mg |
| Lactose | 55 mg |
| sec. Calcium phosphate | 30 mg |
| Soluble starch | 3 mg |
| Magnesium stearate | 5 mg |
| Colloidal silica | 4 mg |
| | 200 mg |

EXAMPLE E

Coated tablets containing an active compound according to the invention and another therapeutically active compound:

| | |
|---|---|
| Active compound | 6 mg |
| Propranolol | 40 mg |
| Lactose | 90 mg |
| Maize starch | 90 mg |
| sec. Calcium phosphate | 34 mg |
| Soluble starch | 3 mg |
| Magnesium stearate | 3 mg |

-continued

| Colloidal silica | 4 mg |
|---|---|
| | 270 mg |

EXAMPLE F

Coated tablets containing an active compound according to the invention and another therapeutically active compound:

| Active compound | 5 mg |
|---|---|
| Pirlindole | 5 mg |
| Lactose | 60 mg |
| Maize starch | 90 mg |
| sec. Calcium phosphate | 30 mg |
| Soluble starch | 3 mg |
| Magnesium stearate | 3 mg |
| Colloidal silica | 4 mg |
| | 200 mg |

EXAMPLE G

Capsules containing an active compound according to the invention and another therapeutically active compound:

| Active compound | 5 mg |
|---|---|
| Nicergoline | 5 mg |
| Maize starch | 185 mg |
| | 195 mg |

EXAMPLE H

Injection solutions containing 1 mg of active compound per ml can be produced using the following formula:

| Active compound | 1.0 mg |
|---|---|
| Polyethylene glycol 400 | 0.3 mg |

-continued

| Sodium chloride | 2.7 mg |
|---|---|
| Water for injections to | 1 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Thienylpiperazines of the general formula I

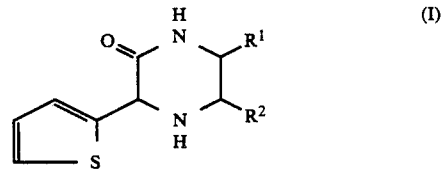

in which $R^1$ denotes hydrogen or double-bonded oxygen and $R^2$ denotes hydrogen or double-bonded oxygen, with $R^1$ and $R^2$ not both having the same meaning, as well as the pharmaceutically tolerated salts thereof.

2. 3-(2-Thienyl)piperazine-2,5-dione and pharmaceutically tolerated salts thereof.

3. 3-(2-Thienyl)piperazine-2,6-dione and pharmaceutically tolerated salts thereof.

4. A process for treating disorders of brain functions or for controlling cerebral aging processes, which comprises administering an effective amount of a thienylpiperazine compound according to claim 1, or a pharmaceutically tolerated salt thereof, to a host in need thereof.

5. Pharmaceutical composition comprising as active compound one or more thienylpiperazine derivatives according to claim 1 or a pharmaceutically tolerated salt thereof together with a pharmaceutically acceptable vehicle and optionally pharmaceutically acceptable additives.

* * * * *